United States Patent
Watanabe et al.

(10) Patent No.: US 9,222,909 B2
(45) Date of Patent: Dec. 29, 2015

(54) BIOSENSOR AND METHOD FOR PRODUCING THE SAME

(71) Applicant: DAI NIPPON PRINTING CO., LTD., Tokyo (JP)

(72) Inventors: Masanao Watanabe, Tokyo (JP); Kenichi Ito, Tokyo (JP); Makoto Ishii, Miyagi (JP); Hiroshi Yoshida, Osaka (JP); Toshiaki Baba, Osaka (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 325 days.

(21) Appl. No.: 13/797,012

(22) Filed: Mar. 12, 2013

(65) Prior Publication Data

US 2013/0192987 A1  Aug. 1, 2013

Related U.S. Application Data

(63) Continuation of application No. PCT/JP2011/070398, filed on Sep. 7, 2011.

(30) Foreign Application Priority Data

Sep. 13, 2010 (JP) .................................. 2010-203899

(51) Int. Cl.
*G01N 27/327* (2006.01)

(52) U.S. Cl.
CPC ........ *G01N 27/3271* (2013.01); *G01N 27/3272* (2013.01)

(58) Field of Classification Search
CPC ...................................... G01N 27/327–27/3272
See application file for complete search history.

(56) References Cited

U.S. PATENT DOCUMENTS 5,427,912 A * 6/1995 Brown et al. .................. 435/7.6
5,565,085 A   10/1996 Ikeda et al.
6,071,391 A * 6/2000 Gotoh et al. ............. 204/403.05

(Continued)

FOREIGN PATENT DOCUMENTS

EP   1314786 A1   5/2003
JP   08-005600 A  1/1996

(Continued)

OTHER PUBLICATIONS

Product Data Sheet for Electrodag 423SS from Acheson (Japan) Limited, downloaded Jun. 9, 2015, publication date unkown. 2 pages.*

(Continued)

*Primary Examiner* — Alexander Noguerola
(74) *Attorney, Agent, or Firm* — Pearne & Gordon LLP (57) ABSTRACT

A biosensor according to the present invention includes a first base material having an insulating surface; an adhesive layer located on the insulating surface of the first base material; and an electrode system and wiring sections fixed to the first base material via the adhesive layer. The electrode system includes top electrode layers and bottom electrode layers, and the bottom electrode layers are formed of a material having a higher conductivity than that of the top electrode layers; the electrode system includes a working electrode and a counter electrode, and also includes an enzyme reaction section located on the working electrode, the enzyme reaction section containing an enzyme and an electron acceptor; and the bottom electrode layers and the wiring sections are integral with each other.

8 Claims, 9 Drawing Sheets (a)

(b)

(56) References Cited

U.S. PATENT DOCUMENTS

| | | | |
|---|---|---|---|
| 6,562,210 B1* | 5/2003 | Bhullar et al. | 204/403.03 |
| 6,662,439 B1* | 12/2003 | Bhullar | 29/825 |
| 6,767,440 B1* | 7/2004 | Bhullar et al. | 204/403.01 |
| 2004/0118704 A1* | 6/2004 | Wang et al. | 205/792 |
| 2008/0211880 A1* | 9/2008 | Hara et al. | 347/70 |
| 2009/0004781 A1* | 1/2009 | Liao et al. | 438/118 |
| 2009/0051606 A1* | 2/2009 | Ochi et al. | 343/702 |
| 2009/0321257 A1 | 12/2009 | Takahara et al. | |
| 2010/0300898 A1 | 12/2010 | Sato et al. | |

FOREIGN PATENT DOCUMENTS

| | | |
|---|---|---|
| JP | 08-015220 A | 1/1996 |
| JP | 2000-131264 A | 5/2000 |
| JP | 2004-004017 A | 1/2004 |
| JP | 2006-275819 A | 10/2006 |
| JP | 2008503728 A | 2/2008 |
| JP | 2008536125 A | 9/2008 |
| JP | 2009204375 A | 9/2009 |
| JP | 2010-032501 A | 2/2010 |
| WO | 0218627 A1 | 3/2002 |
| WO | 2006007451 A1 | 1/2006 |
| WO | 2006110504 A1 | 10/2006 |
| WO | 2009056299 A1 | 5/2009 |
| WO | 2009057793 A1 | 5/2009 |
| WO | 2010004690 A1 | 1/2010 |

OTHER PUBLICATIONS

JPO computer-generated English language translation JP 2006-275819 A downloaded Jun. 9, 2015.*

JPO computer-generated English language translation JP 2010-32501 A downloaded Jun. 9, 2015.*

International Search Report for PCT/JP2011/070398 dated Oct. 25, 2011.

Japanese Office Action dated Feb. 21, 2012 for counterpart Japanese Application JP2010-203899.

Japanese Office Action dated Jul. 3, 2012 for counterpart Japanese Application JP2010-203899.

* cited by examiner

BIOSENSOR AND METHOD FOR PRODUCING THE SAME

CROSS REFERENCE TO RELATED APPLICATIONS

This application is based upon and claims the benefit of priority from the prior Japanese Patent Application No. 2010-203899, filed on Sep. 13, 2010 and PCT Application No. PCT/JP2011/070398, filed on Sep. 7, 2011, the entire contents of which are incorporated herein by reference.

FIELD

The present invention relates to a biosensor, and specifically to a biosensor for performing a measurement on a particular component in a sample with a high level of sensitivity and a method for producing the same.

BACKGROUND

For measuring a concentration or the like of a particular component in a biosample such as blood or the like in a quick and simple manner, a biosensor using electrochemical means has been put into practice. An example of such a biosensor is a glucose sensor for quantifying glucose in the blood electrochemically.

A glucose sensor includes, as basic elements, an electrode system including a working electrode and a counter electrode, an enzyme and an electron acceptor. The enzyme selectively oxidizes glucose in the blood to generate gluconic acid, and also reduces the electron acceptor to generate a reductant. By applying a certain level of voltage to the reductant by the electrode system, the reductant is re-oxidized. At the time of the re-oxidation, an electric current is generated. Since the value of the electric current depends on the concentration of glucose in the blood, the glucose in the blood can be quantified.

According to a conventional biosensor, silver paste is screen-printed to form a lead wire, and conductive carbon paste is printed on the lead wire to form an electrode system (Japanese Laid-Open Patent Publication No. H8-15220 and Japanese Laid-Open Patent Publication No. H8-5600). According to such a conventional biosensor, the electrode system is formed of conductive carbon. Therefore, the resistance of the wire is large, and thus the potential of a surface of the electrode is easily dispersed. This decreases the measuring precision of the glucose concentration. In addition, a surface of the silver paste exposed to air is easily oxidized into silver oxide, which has a high resistance. Therefore, the resistance of the lead wire is not stable.

International Publication WO2010/004690 pamphlet proposes an electrochemical sensor including a conductive layer provided on an insulating base material, a first carbon layer provided on the conductive layer, and a second carbon layer for covering the first carbon layer. The electrochemical sensor described in Patent Document 3 is proposed for the purpose of performing a measurement for a long time and in repetition. This indispensably causes constrains such that, for example, noble metal needs to be used as the material of the conductive layer, especially as the material of a reference electrode, and the conductive layer needs to be formed by vacuum film formation. Production of such an electrochemical sensor has problems of increasing the cost of the material and also increasing the number of production steps. In addition, in order to increase the adhesiveness between the insulating base material and the conductive layer, the conductive layer needs to be formed of Cr, Ti or the like, which is highly adhesive. This further increases the number of production steps and the cost.

SUMMARY

A biosensor for medical use such as a glucose sensor or the like is disposable. A patient uses a new biosensor for each examination. The measurement takes only several seconds to several tens of seconds, and thus the biosensor does not need to have measurement stability for a long time. Such a disposable biosensor is mainly required to (1) have a high level of sensitivity and (2) be produced at low cost with low-cost materials. However, it is difficult to fulfill such requirements by the conventional art described above.

In light of the above-described situation, the present invention has an object of providing a biosensor which measures a concentration or the like of a particular component in a sample with a high level of sensitivity and can be produced at low cost, and a method for producing such a biosensor.

According to an embodiment of the present invention, a biosensor is provided. The biosensor includes a first base material having an insulating surface; an adhesive layer located on the insulating surface of the first base material; and an electrode system and wiring sections fixed to the first base material via the adhesive layer. The electrode system includes top electrode layers and bottom electrode layers, and the bottom electrode layers are formed of a material having a higher conductivity than that of the top electrode layers; the electrode system includes a working electrode and a counter electrode, and also includes an enzyme reaction section located on the working electrode, the enzyme reaction section containing an enzyme and an electron acceptor; and the bottom electrode layers and the wiring sections are integral with each other.

The top electrode layer and the bottom electrode layer formed of a material having a higher conductivity than, namely, a lower resistance value than, that of the top electrode layer are stacked. Owing to this, the resistance value of the electrode system can be significantly decreased as compared with the resistance value of the conventional electrode system, and thus the biosensor can have a high level of sensitivity. In addition, since the bottom electrode layers and the wiring sections are integral with each other, the biosensor has a higher level of sensitivity and can be produced simply.

In the above-described biosensor, the bottom electrode layers and the wiring sections may be formed of the same material. Owing to this, the biosensor can be produced more simply.

In the above-described biosensor, the electrode system may include at least one reference electrode; and the reference electrode may include a top electrode layer and a bottom electrode layer, and the bottom electrode layer may be formed of a material having a higher conductivity than that of the top electrode layer. Owing to this, the resistance value of the electrode system can be significantly decreased as compared with the resistance value of the conventional electrode system, and thus the biosensor can have a high level of sensitivity.

In the above-described biosensor, the working electrode, the counter electrode and the reference electrode may each be formed by covering at least a part of the bottom electrode layer with the top electrode layer. Covering the bottom electrode layer with the top electrode layer contributes to rust-proofing of the bottom electrode layer, and thus prevents direct contact between the enzyme and the bottom electrode layer.

In the above-described biosensor, the top electrode layers may contain carbon; and the bottom electrode layers and the wiring sections may contain either one of aluminum, copper and iron, or an alloy containing at least one of aluminum, copper and iron. The electrode layer, which is formed of one of aluminum, copper and iron, or an alloy containing at least one of aluminum, copper and iron, can be formed thinner than a conventional electrode layer formed of silver paste. Thus, the resistance value of the electrode layer can be suppressed and the level of sensitivity is improved. In addition, covering the bottom electrode layer with the top electrode layer containing carbon contributes to rustproofing of the bottom electrode layer, and thus prevents direct contact between the enzyme and the bottom electrode layer.

In the above-described biosensor, the top electrode layers may contain a carbon pigment and an organic binder; and the top electrode layers may have a thickness of 0.3 μm or greater and 30 μm or less. Since ink containing the conductive carbon pigment and the organic binder is applied to the bottom electrode layer by printing, the top electrode layer can be formed simply. In addition, since the thickness of the top electrode layers is 0.3 μm or greater and 30 μm or less, the enzyme reaction section and the bottom electrode layer having the top electrode layer therebetween can be guaranteed to be spaced apart from each other. Thus, the physical and electrical stability of the electrode layers can be guaranteed.

In the above-described biosensor, the second base material and the third base material may be stacked sequentially above the first base material; the second base material may have a sample supply path leading to an outer edge of the second base material and the working electrode; and the third base material may be fixed to the first base material so as to cover the second base material. Owing to such a structure, the sample supplied from outside can be guided to the working electrode. In addition, since the third base material is fixed to the first electrode so as to cover the second base material, the sample or oxygen supplied from outside is prevented from corroding the bottom electrode layers.

In the above-described biosensor, the biosensor may further include a flow path communicated to the sample supply path and leading to an outer edge of the second base material. Owing to such a structure, when a sample is supplied from outside, the flow path acts as an air discharge flow path to which air in the sample supply path can escape.

According to an embodiment of the present invention, a method for producing a biosensor is provided. The method includes forming an adhesive layer on an insulating surface of a first base material; bonding a metal foil to the adhesive layer and patterning the metal foil to form bottom electrode layers and wiring sections integral with the bottom electrode layers; and forming top electrode layers containing carbon on top surfaces of the bottom electrode layers to form an electrode system including a working electrode and a counter electrode.

The metal foil is bonded to the surface of the first base material via the adhesive layer to form the bottom electrode layers. Therefore, the bottom electrode layers can have a more uniform thickness than the conventional bottom electrode layers formed by printing of silver paste. In addition, since the bottom electrode layers and the wiring sections are integral with each other, the biosensor has a high level of sensitivity and can be produced simply.

In the above-described method for producing a biosensor, the top electrode layers may be formed by partially covering the bottom electrode layers with carbon by printing. Owing to this, the top electrode layers can be formed simply.

In the above-described method for producing a biosensor, a second base material having a sample supply path and an air discharge flow path may be formed by forming the adhesive layer on each of a top surface and a bottom surface of a base material; the second base material and a third base material may be bonded together; and the surface of the first base material on which the electrode system is formed may be bonded to the second base material and the third base material. Owing to this, the sample supplied from outside can be guided to the working electrode. In addition, since the third base material and the second base material are bonded to the first electrode, the sample or oxygen supplied from outside is prevented from corroding the bottom electrode layers.

BRIEF DESCRIPTION OF THE DRAWINGS

FIG. 5(a) is an isometric view of the electrode system 400 as seen from the above, and (b) is a cross-sectional view taken along line A-A' in (a);

FIGS. 8(a) through (d) show steps of forming a second base material 1100 and a third base material 1200, and bonding the electrode system 100 formed on a first base material 170 to the second base material 1100 and the third base material 1200, thereby producing the biosensor 1000, and correspond to cross-sectional views taken along line A-A' in FIG. 2(a); and FIG. 8(e) corresponds to a cross-sectional view taken along line B-B' in FIG. 2(a)

DESCRIPTION OF EMBODIMENTS

Hereinafter, a biosensor and a method for producing the same according to the present invention will be described with reference to the drawings. The biosensor according to the present invention may be carried out in many other forms, and is not to be interpreted as being limited to the following embodiments and examples. In the following embodiments and examples, the same elements or elements having substantially the same functions will bear identical reference signs, and will not be described in repetition.

(1. Structure of Biosensor)

Figure 1:
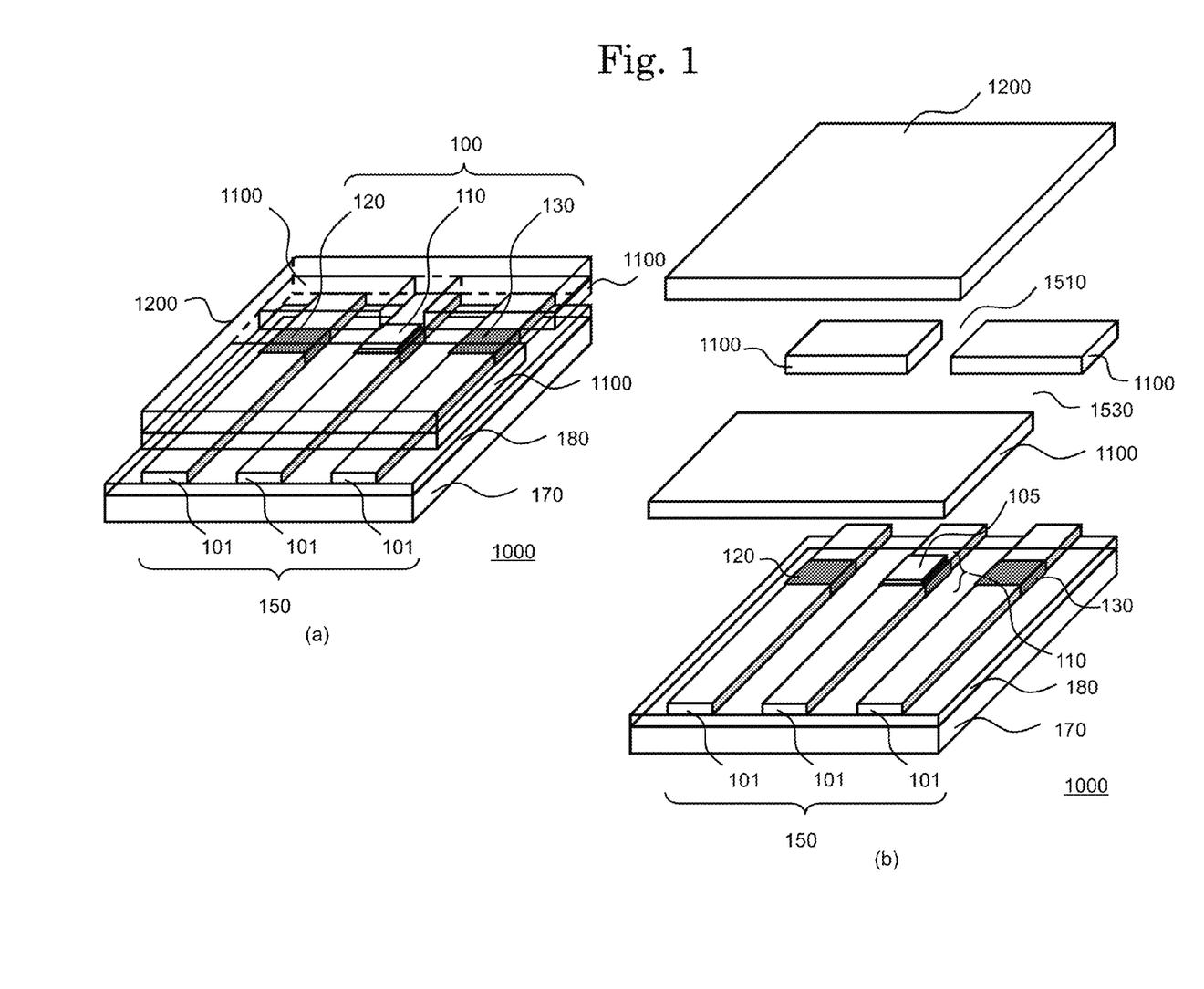
FIG. 1 provides schematic views of a biosensor 1000 in an embodiment according to the present invention; (a) shows the entirety of the biosensor 1000, and (b) is an exploded view of the biosensor.

An electrode structure of a biosensor 1000 in an embodiment according to the present invention will be described. FIG. 1 provides schematic views showing an example of the biosensor 1000 in an embodiment according to the present invention. The biosensor 1000 has the following structure. On an electrode system 100 and wiring sections 150, a second base material 1100 acting as a spacer for forming a sample supply path 1510 is provided and fixed. A third base material 1200 acting as a top cover for the sample supply path 1510 is provided so as to cover the second base material and fixed. FIG. 1(a) shows the entirety of the biosensor 1000. For the simplicity of explanation, the second base material 1100 and the third base material 1200 are shown as being transparent. FIG. 1(b) is an exploded view of the biosensor 1000.

The electrode system 100 includes a working electrode 110, a counter electrode 120 and a reference electrode 130 which are formed on a top surface of a first base material 170. The working electrode 110, the counter electrode 120 and the reference electrode 130 each include a top electrode layer 103 formed in a part of a surface thereof. On a part of a top surface of the top electrode layer 103 of the working electrode 110, an enzyme reaction section 105 is further formed.

The second base material 1100 formed on the electrode system 100 and the wiring sections 150 is located so as to have a T-shaped flow path on the enzyme reaction section 105 on the working electrode 110, the top electrode layer 103 of the counter electrode 120 and the top electrode layer 103 of the reference electrode 130. The T-shaped flow path leads to, for example, an outer edge of the second base material 1100. The T-shaped flow path includes an air discharge flow path 1530 extending straight over the enzyme reaction section 105 on the working electrode 110, the top electrode layer 103 of the counter electrode 120 and the top electrode layer 103 of the reference electrode 130; and a sample supply path 1510 extending perpendicularly to the air discharge flow path 1530 and passing over the enzyme reaction section 105 on the working electrode 110. Owing to the sample supply path 1510 and the air discharge flow path 1530, the biosensor 1000 can utilize the capillary phenomenon of the sample supply path 1510 to allow a measurement sample to pass over the working electrode 110, the counter electrode 120 and the reference electrode 130 and perform a measurement on an intended component of the sample.

Figure 2:
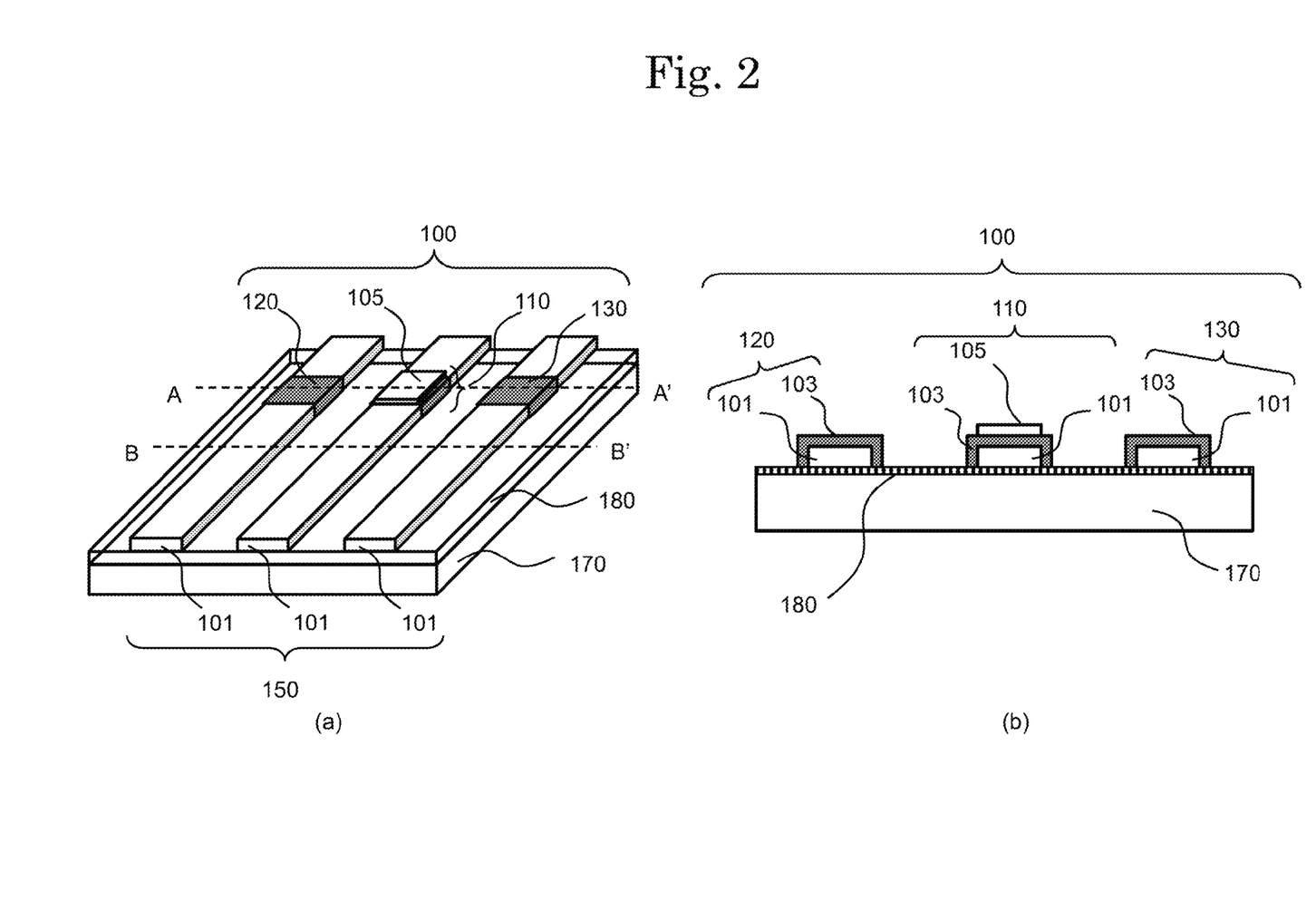
FIG. 2 is provided for explaining an electrode system 100 in the biosensor in the embodiment according to the present invention; (a) is an isometric view of the electrode system 100 as seen from the above, and (b) is a cross-sectional view taken along line A-A' in (a)

FIG. 2 is provided for explaining the electrode system 100 in the biosensor in the embodiment according to the present invention. FIG. 2(a) is an isometric view of the electrode system 100 as seen from the above, and FIG. 2(b) is a cross-sectional view taken along line A-A' in FIG. 2(a). The electrode system 100 according to the present invention includes electrodes each including a stack of the top electrode layer 103 and a bottom electrode layer 101.

The electrodes are fixed to the base material 170 via an adhesive layer 180. In the electrode system 100 in the biosensor in the embodiment according to the present invention, each bottom electrode layer 101 and each wiring section 150 are integral with each other. On at least a part of each bottom electrode layer 101, the top electrode layer 103 is located. Owing to this structure, the biosensor having a high level of sensitivity can be provided in a simple manner. Hereinafter, each of the elements of the biosensor 1000 in the embodiment according to the present invention will be described in detail. In this example, each top electrode layer 103 covers side surfaces of the corresponding bottom electrode layer 101. Alternatively, each top electrode layer 103 may be formed only on a top surface of the corresponding bottom electrode layer 101.

(Base Material)

The first base material 170 supports the electrode system 100, and at least the surface thereof on which the electrode system 100 is located is insulating. The first base material 170 is formed of, for example, a resin base material, a ceramic base material, a glass base material, a semiconductor base material having at least a surface thereof insulated, or a metal base material having at least a surface thereof insulated. The first base material 170 may be rigid or elastic. Among these materials, an elastic material which is electrically insulating is preferable. An example of preferably usable material is a film of a polyethylene terephthalate (PET) resin, a vinyl chloride resin, a polystyrene (PS) resin, a polypropylene (PP) resin or the like. The shape, size and thickness of the first base material 170 may be appropriately set in accordance with the shape or the like of a connection section of a device to which the biosensor according to the present invention is to be connected.

(Electrode System)

As described above, the electrode system 100 includes the working electrode 110, the counter electrode 120 and the reference electrode 130. The working electrode 110 is provided for applying a voltage to an electron acceptor from which a reductant is to be formed. The working electrode 110 includes the bottom electrode layer 101 located on the first base material 170 and the top electrode layer 103 located on the surface of the bottom electrode layer 101. On the top surface of the working electrode 110, the enzyme reaction section 105 is located. The enzyme reaction section 105 may be a mixture of an enzyme and the electron acceptor, or may include the enzyme and the electron acceptor stacked as separate layers. In this embodiment, the enzyme reaction section 105 is directly located on the top surface of the working electrode 110. Alternatively, the enzyme reaction section 105 may be located so as to face the working electrode 110 with a space being held therebetween.

The counter electrode 120 is provided for measuring the value of an electric current flowing by electrons released from the electron acceptor to the working electrode 110. The counter electrode 120 includes the bottom electrode layer 101 located on the top surface of the first base material 170 and the top electrode layer 103 located on the surface of the bottom electrode layer 101.

The reference electrode 130 is used as a reference for determining the potential of the working electrode 110. The reference electrode 130 includes the bottom electrode layer 101 located on the top surface of the first base material 170 and the top electrode layer 103 located on the surface of the bottom electrode layer 101. In the case where the biosensor 1000 in the embodiment according to the present invention is used as a disposable biosensor, the reference electrode 130 may have substantially the same structure as that of the working electrode 110 and the counter electrode 120, and a low-cost metal material such as, for example, one of aluminum, copper and iron or an alloy containing at least one of these materials may be used instead of a noble metal material. Thus, the cost can be decreased. A reason why such a low-cost material is usable is that when the biosensor 1000 is used as a disposable biosensor, the oxidation-reduction potential of the reference electrode 130 in a sample solution is not needed to be especially stable.

Each bottom electrode layer 101 used in the biosensor 1000 in the embodiment according to the present invention is preferably formed of one of aluminum, copper and iron or an alloy containing at least one of these materials. The bottom electrode layer 101 preferably has a thickness in the range of 0.02 µm or greater and 40 µm or less. When the thickness of the bottom electrode layer 101 is less than 0.02 µm, the resistance value of the bottom electrode layer 101 is too high to provide an electrode as intended. When the thickness of the bottom electrode layer 101 exceeds 40 µm, the stacking with the top electrode layer 103 and the formation of the sample supply path 1510 and the air discharge flow path 1530 need to be performed at a high processing precision as required for three-dimensional processing. This significantly increases the number of processing dies, the number of processing steps and the processing time. The bottom electrode layer 101 may be a single layer of any of the above-mentioned metal materials, or may have a stack of a plurality of such metal layers. It is especially preferable that the bottom electrode layer 101 is formed of a metal foil. When being formed of a metal foil, the bottom electrode layer 101 can have a more uniform thickness than when being formed by printing of silver paste as conventionally done. In addition, when a metal foil is patterned by etching, the bottom electrode layer 101 can have a uniform width. The bottom electrode layer 101 in this embodiment is formed of one of aluminum, copper and iron or an alloy containing at least one of these materials, and therefore can be formed to be thinner than a conventional electrode layer formed of silver paste. For this reason, the electrode layer can have a suppressed resistance value and an improved level of sensitivity. Moreover, use of the above-described material allows the top electrode layer 103 containing a carbon pigment to be formed with no surface treatment on the bottom electrode layer 101.

Each top electrode layer 103 is a cover layer formed of a conductive material. The top electrode layer 103 protects the surface of the bottom electrode layer 101 and also acts as a part of the electrode. The top electrode layer 103 may be formed of, for example, a mixture of a carbon pigment and an organic binder. Carbon pigments usable for the biosensor 1000 in the embodiment according to the present invention include, for example, graphite, amorphous carbon, diamond-like carbon, carbon fiber, carbon black, acetylene black, ketjen black (registered trademark), carbon nanotube, carbon nanohorn, carbon nanofiber, and the like. Usable organic binders include acrylic resins, ester resins, vinyl chloride resins, copolymers of vinyl chloride and vinyl acetate, and the like.

In the top electrode layer 103 used in the biosensor 1000 in the embodiment according to the present invention, it is preferable that the carbon pigment is contained in an amount of 5% by weight or greater and 60% by weight or less and that the organic binder is contained in an amount of 10% by weight or greater and 40% by weight or less. When the carbon pigment is contained in an amount of less than 5% by weight, the probability that the carbon pigment particles are electrically connected to each other is significantly decreased, and thus the conductivity of the electrode layer is lost. When the carbon pigment is contained in an amount exceeding 60% by weight, a gap between the pigment particles is enlarged, and thus the physical shape strength, adhesion strength and anti-friction strength are lost. As a result, the required structure and functions cannot be maintained. In addition, the oxidation-reduction state of the surface of the carbon pigment is not stable, and thus the enzyme and the electron acceptor to be added in a later step are adsorbed to the gap non-uniformly. When the organic binder is contained in an amount of less than 10% by weight, the coating characteristic of the top electrode layer 103 is decreased and thus the film strength is also decreased. When the organic binder is contained in an amount exceeding 40% by weight, the coating characteristic of the top electrode layer 103 is decreased and thus the conductivity is also decreased. The top electrode layer 103 may contain an assisting agent, an additive or the like described later.

The top electrode layer 103 preferably has a thickness in the range of 0.3 µm or greater and 30 µm or less. When the thickness of the top electrode layer 103 is less than 0.3 µm, the enzyme reaction section 105 and the bottom electrode layer 101 having the top electrode layer 103 therebetween cannot be spaced apart sufficiently and thus the conditions of production, storage and enzyme reaction cannot be fulfilled and long-term stability cannot be guaranteed. When the thickness of the top electrode layer 103 exceeds 30 µm, there occur problem that, for example, the electrode layer is weakened and the resistance value thereof is increased. The top electrode layer 103 in this embodiment covers the bottom electrode layer 101 with the carbon pigment, which contributes to rustproofing of the bottom electrode layer 101, and thus prevents direct contact between the enzyme and the bottom electrode layer 101. In consideration of rustproofing, it is preferable that the bottom electrode layer 101 is formed of an alloy containing at least one of aluminum, copper and iron. Nonetheless, the bottom electrode layer 101 in this embodiment is sufficiently protected against rust even when being formed of one of aluminum, copper and iron because the bottom electrode layer 101 is covered with the top electrode layer 103.

For forming the top electrode layer 103 in this embodiment, the carbon pigment and the organic binder may be optionally mixed with, for example, any other conductive pigment, a reaction reagent such as a hardening agent or a crosslinker, or an assisting agent or an additive for improving the adaptability to processing. The surface of the top electrode layer 103 may be subjected to, for example, mechanical polishing or physical etching by discharge means such as corona discharge or plasma discharge to improve the activity thereof. In FIG. 2(b), all the electrodes included in the electrode system 100 each include the top electrode layer 103. Such a structure is not absolutely necessary. Depending on the method for supplying the sample, it may be sufficient that only the working electrode 110 includes the top electrode layer 103. Still alternatively, depending on the degree of contact between the sample solution and the bottom electrode layer 101, the top electrode layer 103 may be provided only on the top surface of the bottom electrode layer 101.

Figure 3:
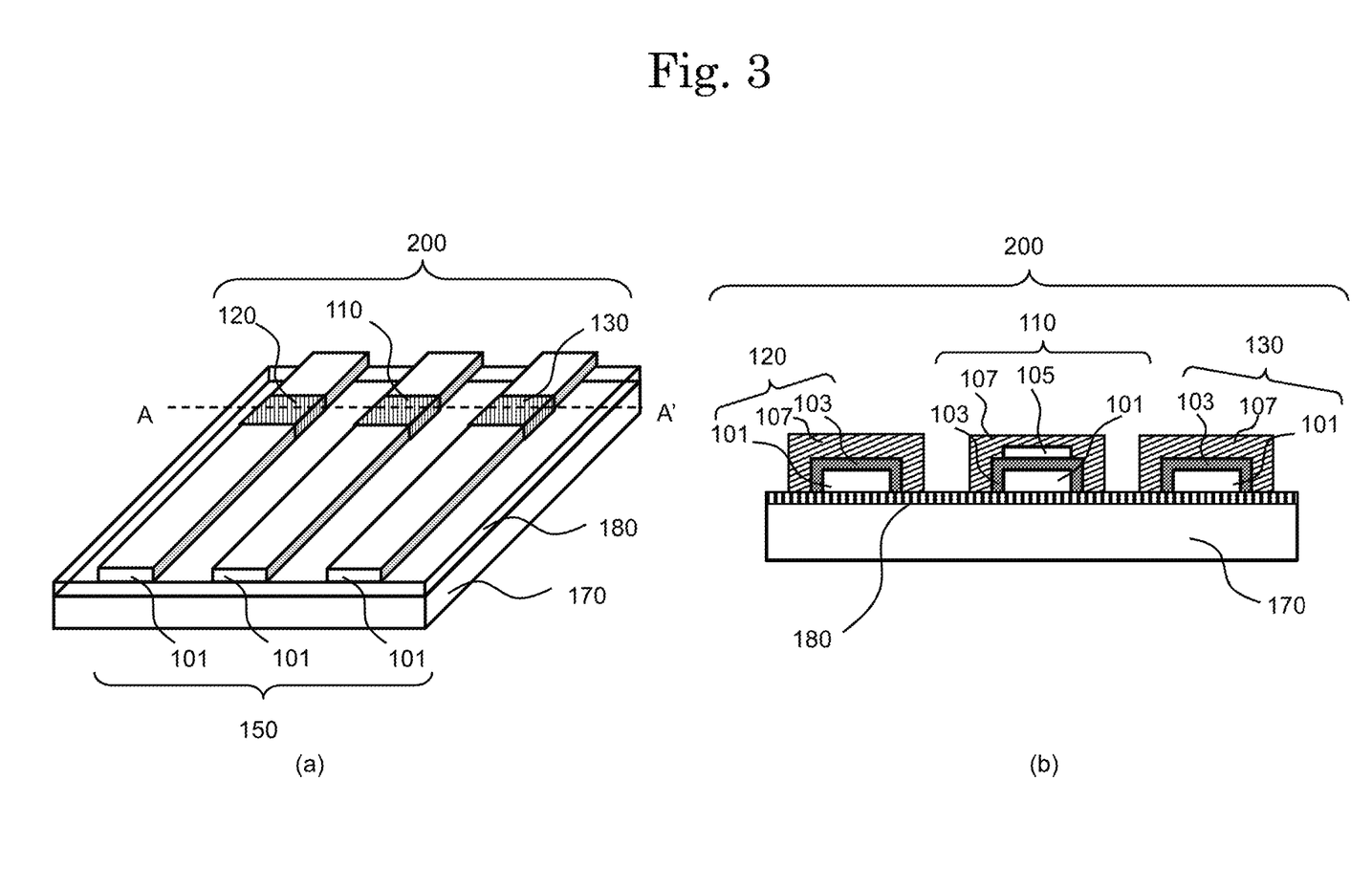
FIG. 3 provides schematic views of an electrode system 200 in a biosensor in an embodiment according to the present invention, the electrode system 200 including hydrophilic polymer layers 107; (a) is an isometric view of the electrode system 200 as seen from the above, and (b) is a cross-sectional view taken along line A-A' in (a)

It is preferable that a hydrophilic polymer layer is formed on the top electrode layer 103. FIG. 3 provides schematic views of an electrode system 200 in a biosensor in an embodiment according to the present invention. The electrode system 200 includes hydrophilic polymer layers 107. FIG. 3(a) is an isometric view of the electrode system 200 as seen from the above, and FIG. 3(b) is a cross-sectional view taken along line A-A' in FIG. 3(a). Regarding each of the counter electrode 120 and the reference electrode 130, the hydrophilic polymer layer 107 is formed on the top electrode layer 103.

Regarding the working electrode 110, the hydrophilic polymer layer 107 is formed on the top electrode layer 103 and the enzyme reaction section 105. In the case where the hydrophilic polymer layers 107 are provided, the blood in contact with the top electrode layer 103 is gelated and thus the response current value is slightly decreased, but the influence of erythrocytes, other proteins and the like on the responsiveness of the sensor can be decreased.

Figure 4:
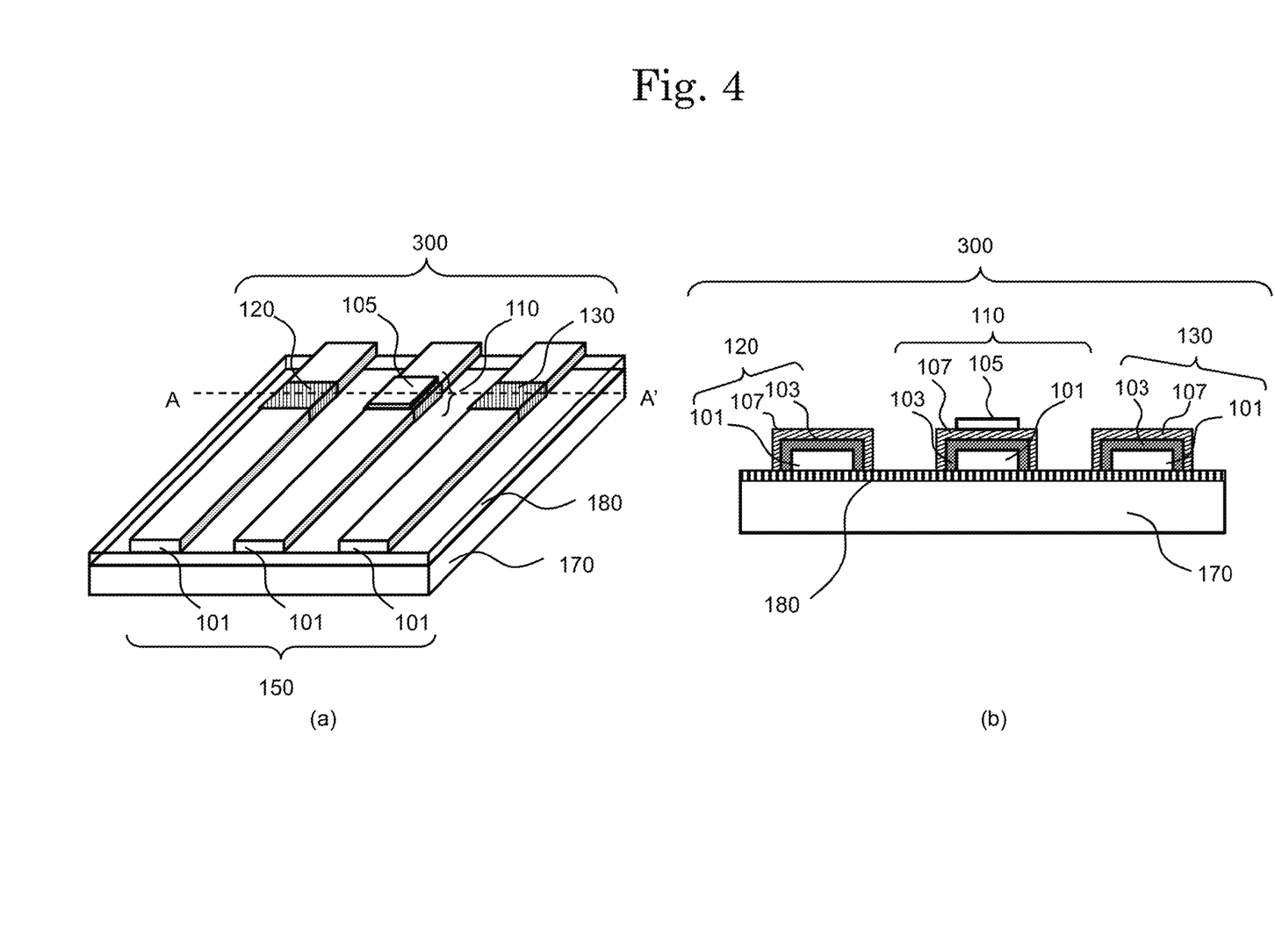
FIG. 4 provides schematic views of an electrode system 300 in a biosensor in an embodiment according to the present invention, the electrode system 300 including hydrophilic polymer layers 107; (a) is an isometric view of the electrode system 300 as seen from the above, and (b) is a cross-sectional view taken along line A-A' in (a)
Figure 5:
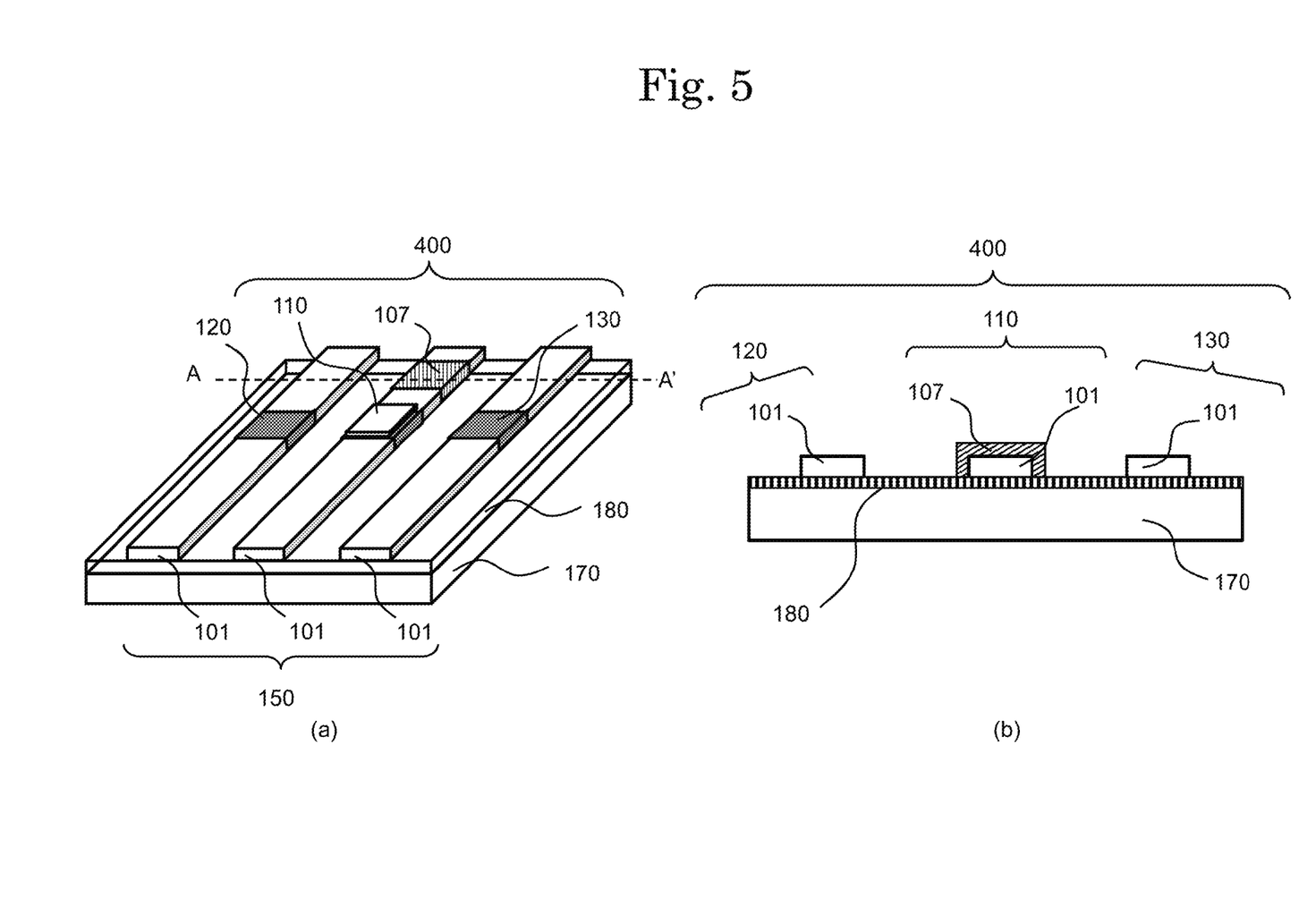
FIG. 5 provides schematic views of an electrode system 400 in a biosensor in an embodiment according to the present invention, the electrode system 400 including hydrophilic polymer layers 107.

FIG. 4 and FIG. 5 show other positioning examples of the hydrophilic polymer layers 107. FIG. 4(a) is an isometric view of an electrode system 300 as seen from the above, and FIG. 4(b) is a cross-sectional view taken along line A-A' in FIG. 4(a). In the electrode system 300, unlike in the electrode system 200, regarding the working electrode 110, the hydrophilic polymer layer 107 is located between the top electrode layer 103 and the enzyme reaction section 105. FIG. 5(a) is an isometric view of an electrode system 400 as seen from the above, and FIG. 5(b) is a cross-sectional view taken along line A-A' in FIG. 5(a). In the electrode system 400, unlike in the electrode system 200, regarding the working electrode 110, the hydrophilic polymer layer 107 is located at a position closer to an opening of the sample supply path 1510 than the top electrode layer 103. In the electrode systems 300 and 400 also, in the case where the hydrophilic polymer layers 107 are provided, the blood is gelated and thus the response current value is slightly decreased, but the influence of erythrocytes, other proteins and the like on the responsiveness of the sensor can be decreased.

Usable hydrophilic polymers include carboxymethyl cellulose, hydroxyethyl cellulose, hydroxypropyl cellulose, ethyl cellulose, methyl cellulose, polyvinylpyrrolidone, polyvinyl alcohol, poly(vinyl acetate), poly(vinyl butyral) and the like, and mixtures thereof. Each hydrophilic polymer layer 107 preferably has a thickness in the range of 50 nm or greater and 2 μm or less. When the thickness of the hydrophilic polymer layer 107 is less than 50 nm, it is difficult to form the hydrophilic polymer layer uniformly. Even if being formed uniformly, the hydrophilic polymer layer is influenced by the ruggedness of the surface of the top electrode layer 103 and thus does not provide the performance which should be provided. When the thickness of the hydrophilic polymer layer 107 exceeds 2 μm, it takes a long time to dissolve the hydrophilic polymer layer 107 and thus the measurement cannot be performed accurately.

The working electrode 110, the counter electrode 120 and the reference electrode 130 are each electrically connected to the wiring section 150 formed integrally with the bottom electrode layer 101. The electrode system 100 and the wiring sections 150 are integral with each other. A voltage can be applied to the electrode system 100, and an electric signal can be drawn out from the electrode system 100, by the wiring sections 150. Since the working electrode 110 and the counter electrode 120 have a stacking structure of a carbon material and a metal material having a lower resistance than that of carbon, the resistance value of the electrode system 100 can be significantly decreased as compared with the conventional electrode system. Thus, the biosensor can have a high level of sensitivity. In addition, since the wiring sections 150 and the electrode system 100 are integral with each other, the level of sensitivity of the biosensor can be further improved. Since it is not necessary to use noble metal for the reference electrode 130, the production cost can be decreased.

(Enzyme Reaction Section)

In the biosensor 1000 in an embodiment according to the present invention, the enzyme reaction section 105 contains an enzyme and an electron acceptor. Enzymes usable for measuring the glucose concentration include glucose oxidase (GOD) and glucose dehydrogenaze (GDH). Electron acceptors usable for measuring the glucose concentration include potassium ferricyanide, ferrocene derivatives, quinone derivatives, osmium derivatives and the like. The enzyme and the electron acceptor are used after being diluted appropriately in a solvent. Solvents usable in this embodiment include, for example, water, alcohol, and a mixture solvent of water and alcohol. Alternatively, the enzyme and the electron acceptor may be uniformly dispersed in straight-chain or cyclic hydrocarbon poor solvent. It is preferable that the enzyme is diluted to 0.3 units or greater and 10 units or less per sample and that the electron acceptor is diluted to 0.5 μg or greater and 200 μg or less per sample. It is preferable that glucose oxidase and glucose dehydrogenaze have a high level of purity. There is no specific limitation on the type of organism from which glucose oxidase and glucose dehydrogenaze are derived as long as the activity in the above-described range is provided. An example of usable glucose oxidase is GLO-201 produced by Toyobo Co., Ltd. The reaction amount of the enzyme and the electron acceptor in the enzyme reaction section 105 is in accordance with the amount of enzyme (titer/unit), but it is sufficient that the reacting dose is a small excess of an optimum part by weight.

It is preferable that the enzyme reaction section 105 is formed to have an area size smaller than that of the top electrode layer 103 and the sample supply path 1510. For example, the enzyme reaction section 105 has a small width in the range of 100 μm or greater and 1000 μm or less. The enzyme reaction section 105 preferably has a thickness in the range of 1 μm or greater and 100 μm or less. The enzyme reaction section 105 provides a detected current value in proportion to the area size thereof, and therefore preferably has an area size as large as possible under the above-mentioned restriction.

The enzyme reaction section 105 may be mixed with a hydrophilic polymer as described above or with a hydrophilic polymer and a surfactant. It is preferable that a surfactant is contained because the surfactant allows even a highly viscous sample solution to be easily guided to the inside of the sensor. Surfactants usable in the enzyme reaction section 105 include, for example, nonionic surfactants, anionic surfactants, cationic surfactants, amphoteric surfactants, polyethylene glycol, and the like. For forming the enzyme reaction section 105, it is preferable that the solvent is dried at 40° C. or lower and after being dried, is returned to room temperature quickly because the enzyme loses activity when being left for a long time at a temperature of 40° C. or higher.

(Second Base Material)

The second base material 1100 is provided for forming a gap between the first base material 170 and the third base material 1200 and providing a flow path for supplying a sample to the biosensor 1000 from outside. The second base material 1100 has at least one sample supply path 1510. The sample supply path 1510 runs through the second base material 1100 in a horizontal direction and guides a sample supplied from outside to the working electrode 110. The second base material 1100 may be rigid or elastic. It is preferable to use an elastic material which is electrically insulating. For example, a film of a polyethylene terephthalate (PET) resin, a vinyl chloride resin, a polystyrene (PS) resin, a polypropylene (PP) resin or the like is preferably usable.

The sample supply path 1510 preferably has a width in the range of 0.5 mm or greater and 5 mm or less. When the width of the sample supply path 1510 is less than 0.5 mm, the supply of the sample to the path performed by use of the capillary phenomenon is not stable. In addition, the area size of the electrode at the enzyme reaction section 105 cannot be large and thus the level of sensitivity is decreased. When the width of the sample supply path 1510 exceeds 5 mm, the following occurs. When the biosensor 1000 is cut in a direction vertical to the surface of the first base material 170 on which the electrode system 100 is formed, the first base material and the third base material are crushed in an arch shape convexed toward the center line in the width direction of the sample supply path 1510. Thus, the capacity of the sample supply path 1510 is easily changed. The sample supply path 1510 may have a uniform width in the entirety thereof, or the width may be increased toward an outer edge of the second base material 1100 from which the sample supply path 1510 is introduced.

The second base material 1100 may further have the air discharge flow path 1530 different from the sample supply path 1510. In the biosensor 1000 in this embodiment, the air discharge flow path 1530 is communicated to the sample supply path 1510. The sample supply path 1510 and the air discharge flow path 1530 form the T-shaped flow path. Owing to such a structure, when a sample is supplied from outside, the air discharge flow path 1530 acts as a path to which air in the sample supply path 1510 can escape. The air discharge flow path 1530 preferably has a width in the range of 0.3 mm or greater and 10 mm or less. When the width of the air discharge flow path 1530 is less than 0.3 mm, an adhesive or burr of the base material obstructs air discharge. When the width of the air discharge flow path 1530 exceeds 10 mm, the following occurs. When the base material is deformed, the adjacent supply path is also deformed, and thus the capacity of the supply path is changed. The thickness of the second base material 1100 is the height of the sample supply path 1510 and the air discharge flow path 1530, and is preferably in the range of 15 µm or greater and 500 µm or less. When the thickness of the second base material 1100 is less than 15 µm, the capacity of the sample supply path 1510 and the air discharge flow path 1530 is easily changed by the influence of the ruggedness of the base material, and the supply of the sample performed by use of the capillary phenomenon is not stable. When the thickness of the second base material 1100 exceeds 500 µm, the sample does not flow to the enzyme reaction section 105 uniformly. Thus, there is a possibility that the sample does not flow to a part of the enzyme reaction section 105.

(Third Base Material)

The third base material 1200 acts as a cover base material. The third base material 1200 may be formed of, for example, a resin base material, a ceramic base material, a glass base material, a semiconductor base material, a metal base material or the like. The third base material 1200 may be rigid or elastic. It is preferable to use an elastic material which is electrically insulating. For example, a film of a polyethylene terephthalate (PET) resin, a vinyl chloride resin, a polystyrene (PS) resin, a polypropylene (PP) resin or the like is preferably usable. The third base material 1200 has a shape in conformity to the shape of the first base material 170, but has a cut-out portion so as to expose the wiring section 150.

(Adhesive Layer)

Each bottom electrode layer 101 in this embodiment is fixed via the adhesive layer 180 formed by applying a dry laminate adhesive on the top surface of the first base material 170. Since the electrode system 100 is fixed to the first base material 170 via the adhesive layer 180, the coherence can be provided without forming a coherence layer on the bottom electrode layer 101. The adhesive layer 180 may be formed of a polyester-based two-component adhesive or the like. The adhesive layer 180 also acts as a stopper in a step of forming the bottom electrode layer 101 by etching a metal layer fixed to the top surface of the first base material 170. The adhesive layer 180 preferably has a thickness in the range of 0.1 µm or greater and 5 µm or less. When the thickness of the adhesive layer 180 is less than 0.1 µm, the adhesive layer 180 cannot provide sufficient adhesion. When the thickness of the adhesive layer 180 exceeds 5 µm, the ruggedness of the adhering surface is conspicuous, the aging time is made long, and tackiness (viscosity of the surface left after the etching or delamination) remains after the etching.

An adhesive layer 185a is formed on a bottom surface of the second base material 1100. In order to bond the second base material 1100 and the third base material 1200 to each other, an adhesive layer 185b is further formed on a top surface of the second base material 1100. The adhesive layer 185b may be formed on a bottom surface of the third base material 1200. The adhesive layers 185a and 185b may be formed of a synthetic adhesive or a natural adhesive. Usable synthetic adhesives include, for example, acrylic-based adhesives, ester-based adhesives, vinyl-based adhesives, silicone-based adhesives and the like. Usable natural adhesives include, for example, glue, natural rubber, starch paste such as sap and the like, natural polymers and the like. Each of the adhesive layers 185a and 185b preferably has a thickness of 3 µm or greater and 50 µm or less. When the thickness of the adhesive layer 185a is equal to or greater than the total thickness of the bottom electrode layer 101, the top electrode layer 103 and the enzyme reaction section 105, for example, about 20 µm, the second base material 1100 and the first base material 170 adhere to each other via the adhesive layers 180 and 185a, and thus the sample supplied from the sample supply path 1510 can be prevented from flowing into the wiring sections 150. In addition, since the adhesive layer 180 and the adhesive layer 185a adhere to each other, the bottom electrode layers 101 integral with the wiring sections 150 can be rustproof.

The third base material 1200 is fixed to the second base material 1100 via the adhesive layer 185b, and is fixed to the first base material 170 via the adhesive layer 180. The adhesive layer 185b may be formed on the bottom surface of the third base material 1200 such that the second base material 1100, the counter electrode 120 and the reference electrode 130 are wrapped with the adhesive layer 185b.

(Positional Relationship of the Sample Supply Path 1510 and the Flow Path 1530 with the Electrode System 100)

Figure 6:
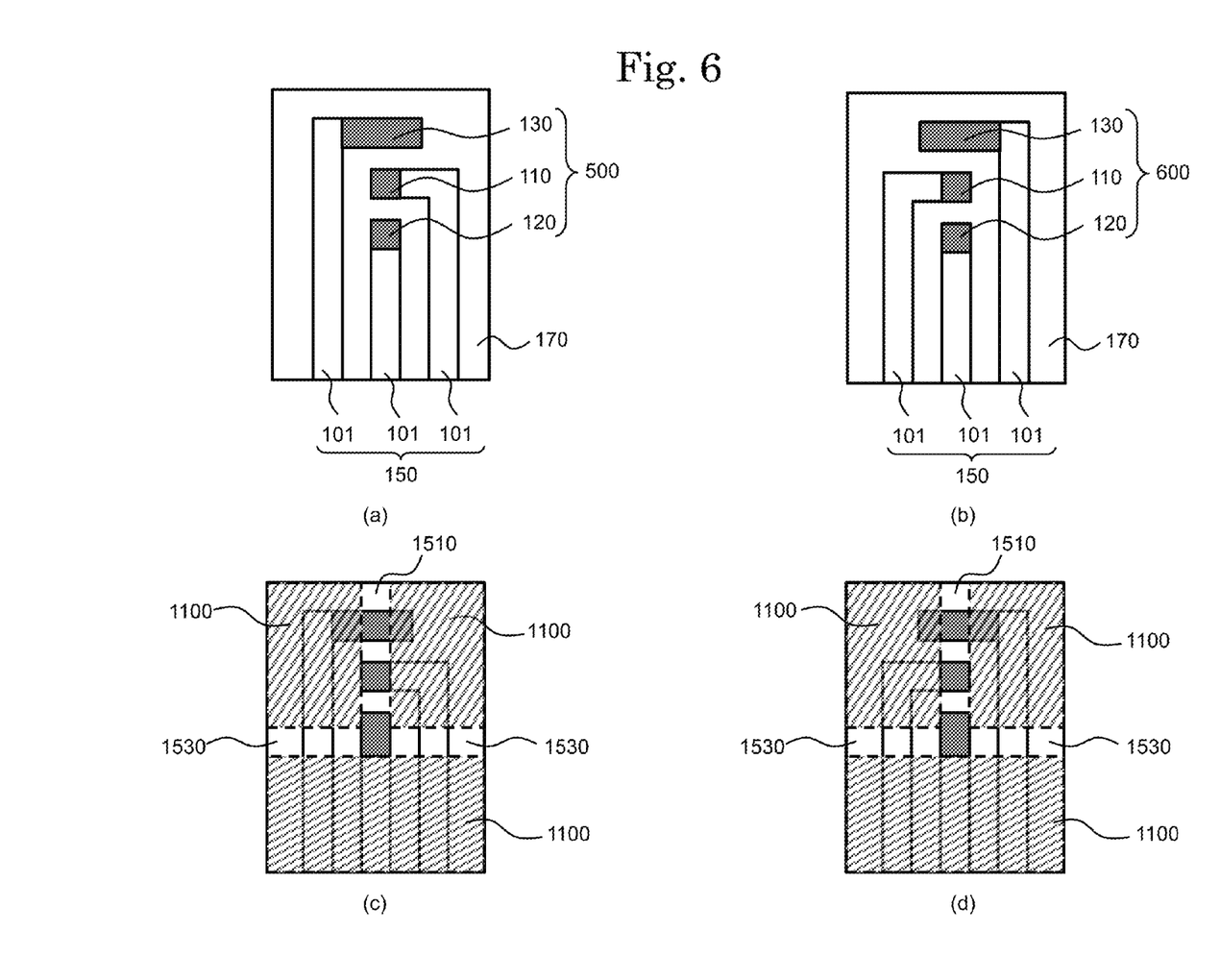
FIG. 6 provides schematic views of an electrode system in a biosensor in an embodiment according to the present invention; (a) shows an electrode system 500, (b) shows an electrode system 600, (c) shows a positional relationship of the sample supply path 1510 and the flow path 1530 with the electrode system 500, and (g) shows a positional relationship of the sample supply path 1510 and the flow path 1530 with the electrode system 600.

The positional arrangement of the electrodes in the electrode system 100 shown in FIG. 1 and FIG. 2 is merely an example, and may be modified in various manners. Now, with reference to FIG. 6, another embodiment of preferable positional relationship of the sample supply path 1510 and the flow path 1530 with the electrode system 100 will be described. FIG. 6(a) shows an electrode system 500, and FIG. 6(b) shows an electrode system 600. FIG. 6(c) shows a positional relationship of the sample supply path 1510 and the flow path 1530 with the electrode system 500, and FIG. 6(g) shows a positional relationship of the sample supply path 1510 and the flow path 1530 with the electrode system 600. The electrode system 500 and the electrode system 600 are located symmetrically with respect to the center line in the width direction of the sample supply path 1510. The reference electrode 130, the working electrode 110 and the counter electrode 120 may be located such that a sample passes these electrodes sequentially from the opening of the sample supply path 1510. Owing to such a positional arrangement, it can be confirmed that the electrode system is filled with the sample by the voltage value or the current value of a potentiostat. Since the working electrode 110 is located between the reference electrode 130 and the counter electrode 120, the potential interference is unlikely to occur. When the counter electrode 120 is filled with the sample, the reference electrode 130 and the working electrode 110 have a potential. Therefore, the influence of the initial noise is unlikely to be exerted, and the measurement can be stabilized.

By changing the type of enzyme in the enzyme reaction section 105, the biosensor 1000 in an embodiment according to the present invention can be made usable for a wide range of reaction systems related to an enzyme, including a cholesterol sensor, an alcohol sensor, a sucrose sensor, a lactic acid sensor, a fructose sensor and the like as well as a glucose sensor. The enzyme usable for each type of biosensor is cholesterol esterase, cholesterol oxidase, alcohol oxidase, lactate oxidase, fructose dehydrogenase, xanthine oxidase, amino acid oxidase or the like which is suitable to the respective reaction system.

(2. Method for Producing the Biosensor)

Figure 7:
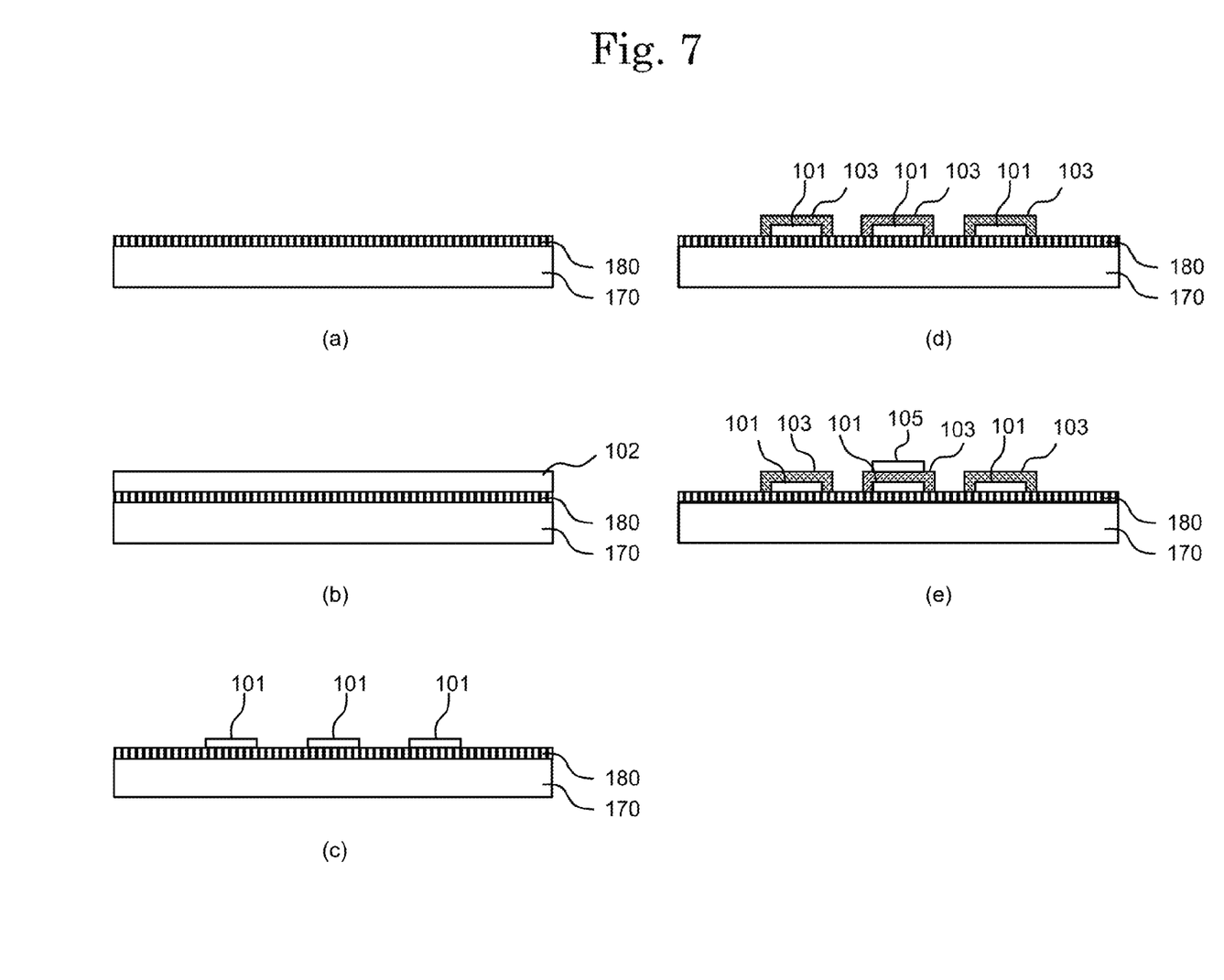
FIG. 7 is provided for explaining a method for producing the biosensor 1000 in an embodiment according to the present invention; (a) through (e) show steps for producing the biosensor 1000 and correspond to cross-sectional views taken along line A-A' in FIG. 2(a)
Figure 8:
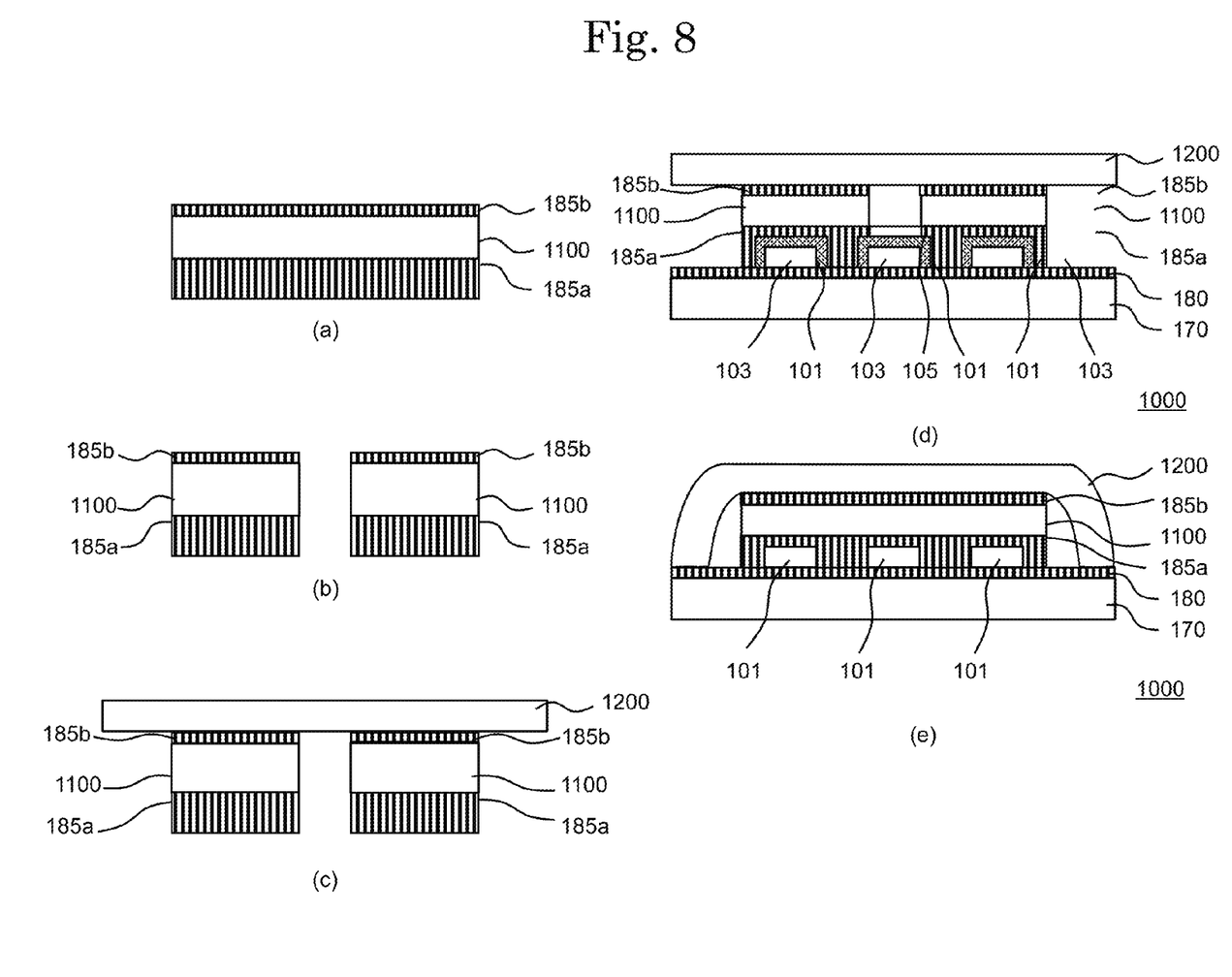
FIG. 8 is provided for explaining the method for producing the biosensor 1000 in the embodiment according to the present invention.

Now, with reference to FIG. 7 and FIG. 8, a method for producing the biosensor 1000 described in the above embodiments will be described. FIGS. 7(a) through 7(e) show steps for producing the biosensor 1000 and correspond to cross-sectional views taken along line A-A' in FIG. 2(a).

(Step of Producing the Electrode System)

The adhesive layer 180 is located on the top surface of the first base material 170 (FIG. 7(a)). The adhesive layer 180 may be formed by applying an adhesive or may be bonded to the first base material 170. A metal foil 102 is bonded to the first base material 170 via the adhesive layer 180 (FIG. 7(b)). On the metal foil 102, a resist (not shown) is formed by coating, printing or the like, and formed into a desired resist pattern. The metal foil 102 is etched by use of the resist pattern as an etching mask to form the bottom electrode layers 101 (FIG. 7(c)). The etching may be either dry etching or wet etching. The bottom electrode layers 101 adhere to the first base material 170 via the adhesive layer 180. Therefore, the bottom electrode layers 101 can be formed more simply with no need to form a coherence layer on the bottom electrode layers 101. In addition, the metal foil having a highly uniform thickness is bonded and patterned to form the bottom electrode layers 101. Therefore, when a plurality of chips are formed on one first base material, the sensitivity dispersion among the chips is suppressed. The bottom electrode layers 101 may be formed by vacuum film formation or plating, but these methods are not preferable. With such methods, as the first base material 170 becomes larger, the in-plane thickness dispersion of the bottom electrode layers 101 is made larger. As a result, the level of sensitivity is dispersed among the chips.

After the above-described step, ink containing conductive carbon is applied to a prescribed part of each bottom electrode layer 101 by printing (FIG. 7(d)). In order to prevent generation of pin holes, it is preferable that the ink is applied at least a plurality of times. As a result, the top electrode layers 103 each for covering at least the top surface of the corresponding bottom electrode layer 101 are formed. More preferably, the top electrode layers 103 are each formed to cover the top surface and side surfaces of the corresponding bottom electrode layer 101.

Regarding one of the electrodes thus formed, a solution containing an enzyme and an electron acceptor is applied with a dispenser to the top surface of the top electrode layer 103, and is dried at 40° C. to remove the solvent component. As a result, the working electrode 110 is formed (FIG. 7(e)). Thus, the electrode system 100 is produced.

(Step of Producing the Second Base Material)

FIGS. 8(a) through 8(d) show steps of forming the second base material 1100 and the third base material 1200, and bonding the electrode system 100 formed on the first base material 170 to the second base material 1100 and the third base material 1200, thereby producing the biosensor 1000. On the surface of the second base material 1100 to which the first base material 170 and the electrode system 100 are to be bonded, and also on the surface of the second base material 1100 to which the third base material 1200 is to be bonded, the adhesive layer 185 is formed (FIG. 8(a)). The base material 1100 having the adhesive layer 185 formed on both of the top surface and the bottom surface thereof is punched to form the sample supply path 1510 and the air discharge flow path 1530. Thus, the second base material 1100 is formed (FIG. 8(b)).

(Step of Producing the Third Base Material)

The base material 1200 is punched as prescribed to form the cut-out portion, which exposes at least a part of each wiring section 150. Thus, the third base material 1200 is produced.

(Step of Bonding)

To one of the surfaces of the second base material 1100, the third base material 1200 is bonded (FIG. 8(c)). Then, to the other surface of the second base material 1100, the first base material 170 is bonded such that the second base material 1100 and the electrode system 100 face each other (FIGS. 8(d) and 8(e)). FIG. 8(d) corresponds to a cross-sectional view taken along line A-A' in FIG. 2(a). In FIG. 8(d), the sample supply path 1510 and the air discharge flow path 1530 are formed. In the cross-section taken along line A-A', the air discharge flow path 1530 is open outward. FIG. 8(e) corresponds to a cross-sectional view taken along line B-B' in FIG. 2(a). Both ends of the first base material 170 and the second base material 1100 are bonded together via the adhesive layer 180 and the adhesive layer 185. The third base material 1200 may be bonded to the second base material 1100 after the second base material 1100 and the first base material 170 are bonded together.

(Step of Cutting)

The above-described steps are performed in the state where a plurality of biosensors are produced using one first base material 170. After the bonding step is completed, the assembly of the elements is divided into individual biosensors 1000.

EXAMPLES

In the following, examples of the biosensor 1000 according to the present invention described in the above embodiments will be specifically described.

Example 1

Bottom Electrode Layer of Aluminum

On the top surface of the base material 170 formed of a PET film having a thickness of 100 μm (Lumirror produced by Toray Industries Inc.), the adhesive layer 180 was formed by use of a dry laminate agent. An aluminum film 102 having a thickness of 9 μm (produced by Toyo Aluminum K.K.) was bonded to the base material 170 via the adhesive layer 180. On a surface of the aluminum film 102, a linear resist pattern having a width of 1.5 mm was formed by printing. The resultant stacking film with the resist pattern was immersed in a swing-type hydrochloric acid tank (2 N) to etch the aluminum film. After being washed with water, the resultant stacking film was immersed in a sodium hydroxide tank (0.5 N) to remove the resist pattern. Then, the resultant stacking film was washed with water again. Thus, the bottom electrode layer 101 was formed.

On the aluminum pattern of the bottom electrode layer 101, a screen printing pattern 150 mesh having a width of 2.1 mm and a length of 3 mm was aligned with respect to the center line in the width direction of the base material 170 such that about a width of 0.3 mm of the screen printing pattern would cover an area outer to one edge of the surface of the bottom electrode layer 101 and about a width of 0.3 mm of the screen printing pattern would cover an area outer to the other edge of the surface of the bottom electrode layer 101. Low resistance carbon screen ink (produced by Jujo Ink) was printed and dried at 90° C. for 1 hour. From the difference between the level of the top electrode layer 103 formed by covering the bottom electrode layer 101 with carbon and the level of the bottom electrode layer 101 formed of the aluminum pattern, the thickness of the top electrode layer 103 was found to be 11 μm. From this assembly of the top electrode layer 103 and the bottom electrode layer 101, a portion having a total length of 33 mm in the longitudinal direction of the bottom electrode layer 101 was cut from the tip of the top electrode layer 103. This portion included the top electrode layer 103 and a part of the bottom electrode layer 101 formed of aluminum which was not covered with the top electrode layer 103. The resistance value between the tip of the top electrode layer 103 and a position of the bottom electrode layer 101 which was distanced from the tip of the top electrode layer 103 by 30 mm was measured to be 50Ω.

Example 2

Bottom Electrode Layer of Aluminum

Like in Example 1, on the aluminum pattern of the bottom electrode layer 101 having a width of 1.5 mm, a film mask having a width of 2.1 mm and a length of 3 mm (produced by Hitachi Chemical Co., Ltd.) was aligned with respect to the center line in the width direction of the base material 170 such that about a width of 0.3 mm of the film mask would cover an area outer to one edge of the surface of the bottom electrode layer 101 and about a width of 0.3 mm of the film mask would cover an area outer to the other edge of the surface of the bottom electrode layer 101. Carbon gravure ink (produced by Godo Printing Ink Mfg. Co., Ltd.) was printed and dried at 120° C. for 10 minutes. From the difference between the level of the top electrode layer 103 formed by covering the bottom electrode layer 101 with carbon and the level of the bottom electrode layer 101 formed of the aluminum pattern, the thickness of the top electrode layer 103 was found to be 2 μm. From this assembly of the top electrode layer 103 and the bottom electrode layer 101, a portion having a total length of 33 mm in the longitudinal direction of the bottom electrode layer 101 was cut from the tip of the top electrode layer 103. This portion included the top electrode layer 103 and a part of the bottom electrode layer 101 formed of aluminum which was not covered with the top electrode layer 103. The resistance value between the tip of the top electrode layer 103 and a position of the bottom electrode layer 101 which was distanced from the tip of the top electrode layer 103 by 30 mm was measured to be 20Ω.

Example 3

Bottom Electrode Layer of a Metal Material other than Aluminum

In this example, unlike in Example 1, the bottom electrode layer 101 was formed of a copper foil (produced by Nikkan Industries Co., Ltd.) having a thickness of 18 μm. An assembly provided by bonding such a bottom electrode layer 101 to a PET film having a thickness of 50 μm with an adhesive layer having a thickness of 23 μm was used. The resist pattern was etched with an etchant formed of ferric chloride for thin copper foils. Washing with water, resist removal and drying were performed as in Example 1 to form the bottom electrode layer 101. The top electrode layer 103 was formed of carbon by screen printing so as to cover the bottom electrode layer 101. From the difference between the level of the top electrode layer 103 formed by covering the bottom electrode layer 101 with carbon and the level of the bottom electrode layer 101 formed of the copper pattern, the thickness of the top electrode layer 103 was found to be 11 μm. From this assembly of the top electrode layer 103 and the bottom electrode layer 101, a portion having a total length of 33 mm in the longitudinal direction of the bottom electrode layer 101 was cut from the tip of the top electrode layer 103. This portion included the top electrode layer 103 and a part of the bottom electrode layer 101 formed of copper which was not covered with the top electrode layer 103. The resistance value between the tip of the top electrode layer 103 and a position of the bottom electrode layer 101 which was distanced from the tip of the top electrode layer 103 by 30 mm was measured to be 40Ω.

Comparative Example 1

In a comparative example, on a PET film having a thickness of 100 μm (Lumirror produced by Toray Industries Inc.), a linear carbon screen printing pattern 150 mesh having a width of 1.5 mm was provided, and low resistance carbon screen ink (produced by Jujo Ink) was printed and dried at 90° C. for 1 hour. Thus, an electrode layer was formed. A portion having a total length of 33 mm was cut out. The resistance value between positions on the surface of the carbon which were away from each other by 30 mm was measured to be 1.5 KΩ.

(Glucose Detection Characteristic)

Figure 9:
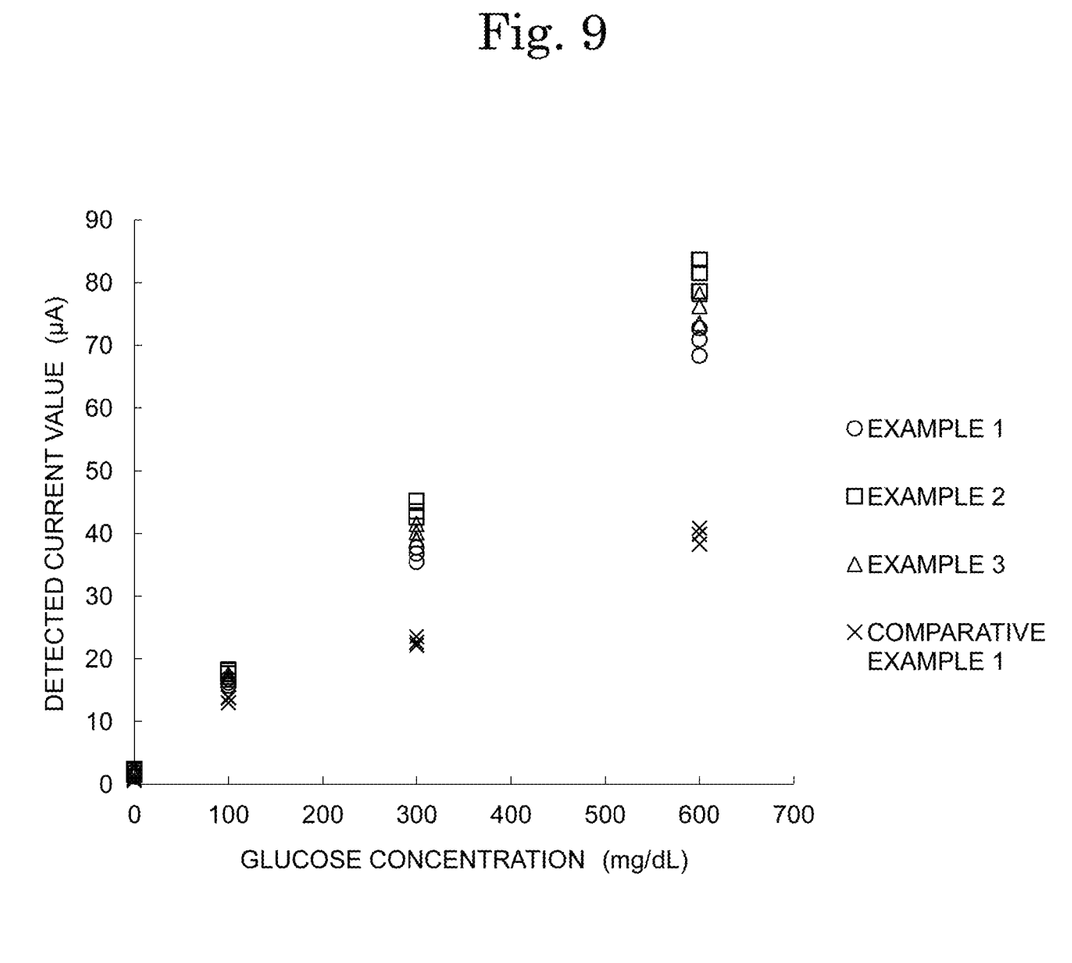
FIG. 9 shows a glucose detection characteristic of the biosensor 1000 in an example according to the present invention.

By use of the electrodes in Examples 1 through 3 and Comparative example 1 obtained as described above, the working electrode 110, the counter electrode 120 and the reference electrode 130 were located at a pitch of 2.4 mm. The electrode layer was 3 mm long. A tip portion having a length of 2.4 mm of the electrode layer was kept exposed, and a tip side portion of 0.3 mm and a back side portion of 0.3 mm were masked with a water-resistant adhesive tape. One unit of glucose oxidase (GLO-201 produced by Toyobo Co., Ltd.) and 70 μg of potassium ferricyanide as the electron acceptor were dissolved in 2 ηL of distilled water and uniformly dropped to the inter-mask portion having a width of 2.4 mm. Thus, the working electrode was produced. These electrodes were wired to a working electrode, a counter electrode and a reference electrode of a potentiostat (ALD760 produced by ABS). A voltage of 0.5 V was applied. Two seconds after 2.5 μL of each of samples was dropped, the current value was detected. The samples were artificial standard glucose solutions prepared by mixing glucose in a physiological saline solution at four concentration levels of 0, 100, 300, and 600 mg/dL. The measurement sensitivity of the glucose concentration was measured. As shown in FIG. 9, in Example 1 and Example 2, the detected current value was higher than in Comparative example 1 for the same concentration of glucose. It was confirmed that the level of measurement sensitivity is improved by use of the electrode system 100 including the top electrode layer 103 formed of carbon and the bottom electrode layer 101 formed of a low resistance metal layer.

According to the present invention, a concentration or the like of a particular component in a sample can be measured with sensitivity. Also according to the present invention, a biosensor which can be produced at low cost and a method for producing such a biosensor are provided.

The invention claimed is:

1. A biosensor, comprising:
a first base material having an insulating surface;
a first adhesive layer located on the insulating surface of the first base material; and
an electrode system and wiring sections fixed to the first base material via the adhesive layer;
wherein:
the electrode system includes top electrode layers and bottom electrode layers, and the bottom electrode layers are formed of a material having a higher conductivity than that of the top electrode layers;
the electrode system includes a working electrode and a counter electrode, and also includes an enzyme reaction section located on the working electrode, the enzyme reaction section containing an enzyme and an electron acceptor;
the bottom electrode layers and the wiring sections are integral with each other,
each of the top electrode layers contains a carbon pigment and an organic binder and each of the top electrode layers has a thickness of 0.3 μm or greater and 2 μm or less, and
each of the top electrode layers covers at least a part of a top surface and side surfaces of each of the bottom electrode layers, respectively.

2. The biosensor according to claim 1, wherein the bottom electrode layers and the wiring sections are formed of the same material.

3. The biosensor according to claim 1, wherein:
the electrode system includes at least one reference electrode;
the reference electrode includes a top electrode layer and a bottom electrode layer, and the bottom electrode layer is formed of a material having a higher conductivity than that of the top electrode layer,
the top electrode layer contains a carbon pigment and an organic binder and the top electrode layer has a thickness of 0.3 μm or greater and 2 μm or less, and
the top electrode layer covers at least a part of a top surface and side surfaces of the bottom electrode layer.

4. The biosensor according to claim 1, wherein:
the top electrode layers contain carbon; and
the bottom electrode layers and the wiring sections contain either one of aluminum, copper and iron, or an alloy containing at least one of aluminum, copper and iron.

5. The biosensor according to claim 1, wherein:
a second base material and a third base material are stacked sequentially above the first base material;
the second base material has a sample supply path leading to an outer edge of the second base material and the working electrode; and
the third base material is fixed to the first base material so as to cover the second base material.

6. The biosensor according to claim 5, further comprising a flow path communicated to the sample supply path and leading to an outer edge of the second base material.

7. The biosensor according to claim 5, further comprising a second adhesive layer bonding the first base material and the second base material and a third adhesive layer bonding the second base material and the third base material,
wherein the first base material and the second base material adhere to each other via the first adhesive layer and the second adhesive layer,
the third base material is fixed to the first base material via the first adhesive layer so as to cover the second base material.

8. The biosensor according to claim 1, the electrode layers are formed by printing a carbon gravure ink containing the carbon pigment and the organic binder.

* * * * *